US00PP26902P3

(12) United States Plant Patent
Banados Ortiz et al.

(10) Patent No.: US PP26,902 P3
(45) Date of Patent: Jul. 5, 2016

(54) BLACKBERRY PLANT NAMED 'EMILIA'

(50) Latin Name: ***Rubus* subgenus *Rubus***
Varietal Denomination: Emilia

(75) Inventors: Maria Pilar Banados Ortiz, San Fernando (CL); Alejandra Andrea Salgado Rojas, Santiago (CL); Jessica Maria Gonzalez Mahan, Santiago (CL); John Reuben Clark, Fayetteville, AR (US)

(73) Assignee: Hortifrut, S.A., Santiago (CL)

( * ) Notice: Subject to any disclaimer, the term of this patent is extended or adjusted under 35 U.S.C. 154(b) by 247 days.

(21) Appl. No.: 13/568,018

(22) Filed: Aug. 6, 2012

(65) Prior Publication Data

US 2014/0041087 P1 Feb. 6, 2014

(51) Int. Cl.
*A01H 5/08* (2006.01)

(52) U.S. Cl.
USPC ..... Plt./203
CPC ..... *A01H 5/0887* (2013.01)

(58) Field of Classification Search
USPC ..... Plt./203
See application file for complete search history.

(56) References Cited

U.S. PATENT DOCUMENTS

| | | | | |
|---|---|---|---|---|
| PP6,679 | P | 3/1989 | Moore | |
| PP6,782 | P | 5/1989 | Jennings | |
| PP8,510 | P | 12/1993 | Moore | |
| PP11,865 | P2 | 5/2001 | Clark et al. | |
| PP13,525 | P3 | 1/2003 | Fear | |
| PP17,983 | P2 * | 9/2007 | Cabrera Avalos | Plt./203 |
| PP20,891 | P3 | 3/2010 | Clark | |
| PP22,002 | P2 * | 7/2011 | Sills et al. | Plt./203 |

OTHER PUBLICATIONS

Clark, John R. et at., "Blackberry Breeding and Genetics," Plant Breeding Reviews. vol. 29, pp. 19-144, John Wiley & Sons, Inc., 2007.

* cited by examiner

*Primary Examiner* — Keith Robinson
(74) *Attorney, Agent, or Firm* — King IP Law; Joshua King

(57) ABSTRACT

A new and distinct cultivar of Blackberry plant named 'Emilia' as described and shown herein. Distinctive characteristics of 'Emilia' include its earliness, thornless stems, large sized fruit and sweetness without bitter aftertaste.

3 Drawing Sheets

Figure 1:
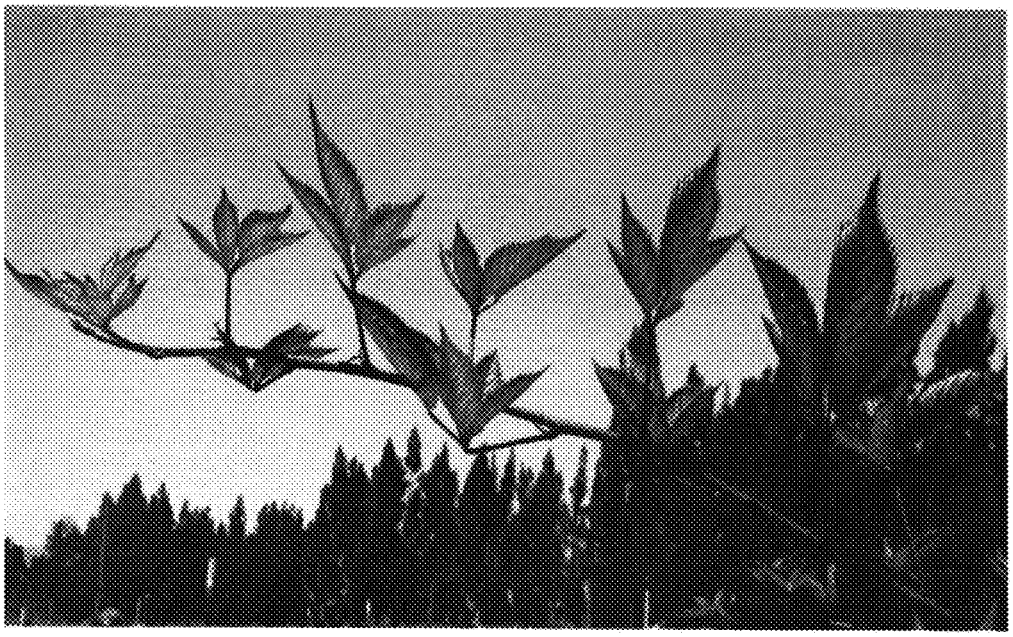

Botanical name of the claimed plant: Family: Rosaceae. Botanical name: *Rubus* subgenus *Rubus*. Common name: Blackberry.

Cultivar name of the claimed plant: 'Emilia'.

BACKGROUND AND SUMMARY

Blackberries are a well-known, aggregate fruit enjoyed by many throughout the world. One example of an existing blackberry variety is 'Tupy', which is a publicly available variety not subject to patent. Another example of an existing, patented blackberry variety is ' Navaho', U.S. Plant Pat. No. 6,679.

Compared to 'Tupy', the present cultivar, 'Emilia', does not have spines, and the fruits are smaller than 'Tupy' (6.1 grams versus 8.0 grams, average). However, the fruits of 'Emilia' are longer (2.8 versus 2.4 cm) than 'Tupy'. In addition, while the acidity and sugar content of the fruits are similar, 'Emilia' does not have the bitter aftertaste that 'Tupy' has. The fruits of 'Emilia' ripen about one week before 'Tupy'.

Compared to 'Navaho', the present cultivar, 'Emilia', has vegetative vigor much higher than 'Navaho'. In the experimental garden in Nogales, Fifth Region, Chile, where both varieties were grown and evaluated, the fruit of 'Emilia' was much larger (6.1 g v/s 3.0 g) and longer (2.8 cm v/s 1.5 cm). Fruit of 'Emilia' has more acidity and less soluble solids than 'Navaho'. 'Emilia' ripens 5 weeks before 'Navaho'.

Distinctive characteristics of 'Emilia' include its earliness, thornless stems, large sized fruit and sweetness without bitter aftertaste.

BRIEF DESCRIPTION OF THE PHOTOGRAPHS

FIG. 1 is a photograph of a primocane of the Blackberry cultivar 'Emilia', showing the purple coloration and absence of thorniness of the stems. This picture was taken three months after primocane emergence, but the section of the primocane shown is about one month's growth (photo taken 9 Feb. 2012).

Figure 2:
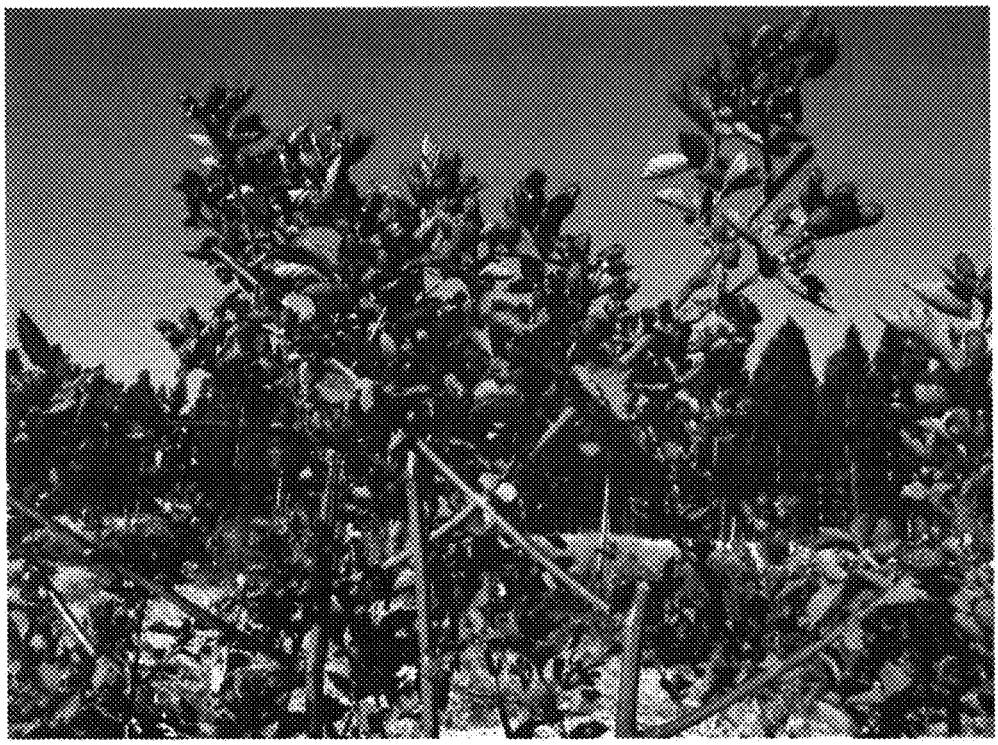

FIG. 2 is a photograph of fruiting laterals, this picture demonstrates the high productivity of the Blackberry cultivar 'Emilia'. This picture was taken on 12 Dec. 2011 and shows floricanes that are about 15 months old at the time of the photo (note: the floricanes had been pruned in January 2011 at about 1.2 m height in order to stimulate the breaking of the laterals. (*Eucalyptus globulus* trees in the background.)

Figure 3:
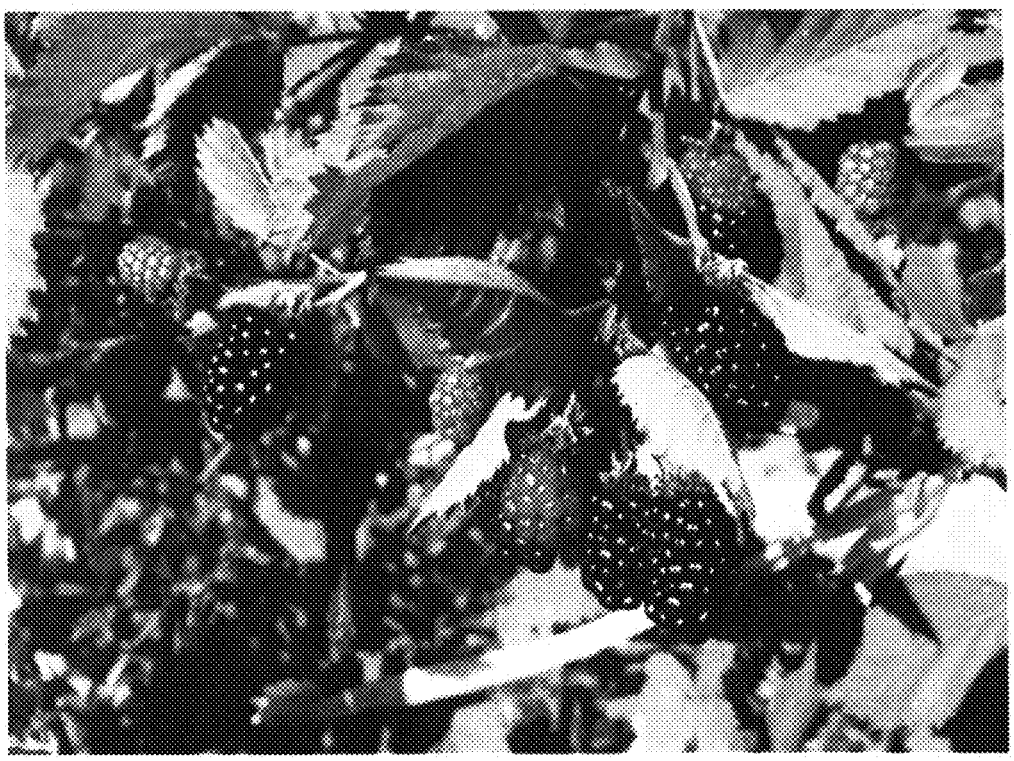

FIG. 3 is a close-up photograph of ripe and unripe fruit on floricanes of the Blackberry cultivar 'Emilia'. Photograph taken 12 Dec. 2011. These pictures were taken between 40 and 50 days after petal fall, with the black fruits being closer to 50 days, and the red fruits being closer to 40 days.

DETAILED DESCRIPTION

Note: statements of characteristics herein represent exemplary observations of the cultivar herein and will vary depending on time of year, location, annual weather, etc. Where dimensions, sizes, colors, and other characteristics are given, it is to be understood that such characteristics are approximations and averages. The descriptions reported herein are from specimen plants that were two years old and were planted in August 2009 at Nogales, Fifth Region, Chile.

Cultivar name: 'Emilia'.

Classification:

*Family*.—Rosaceae.

*Botanical name*.—*Rubus* subgenus *Rubus*.

*Common name*.—Blackberry.

Parentage:

*Female parent*.—Name: 'A-2240T'. This was a proprietary breeding line that was never patented and was discarded in 2008. The cane habit of 'A-2240T' was erect to semi-erect and it ripened in the early season, near Arapaho (U.S. Plant Pat. No. 8,510) and Natchez (U.S. Plant Pat. No. 20,891). 'A-2240T', therefore, likely would have ripened somewhat earlier than 'Emilia' had they been compared in the same site. 'A-2240T' had long, heavy berries, weighing about 8 g. 'A-2240T' was a sibling of Natchez.

*Male parent*.—Name: 'A-1689T'. This was a proprietary breeding line that was never patented and was discarded. 'A-1689T' ripens much later than 'Emilia', mid-late season, near 'Navaho' (U.S. Plant Pat. No. 6,679) and Apache (U.S. Plant Pat. No. 11,865). 'A-1689T' has large berries, 7-8 g, that are medium elongated but not extended long shape.

The cross between the parents was made near Clarksville, Ark., USA in 2005 and resulted from a controlled hand pollination of female parent 'A-2240T'×'A-1689T' male parent. Seeds from this controlled pollination were then sent to a nursery at Hijuelas, Fifth Region, Chile in September 2005. These seeds were germinated in a greenhouse between November 2005 and March 2006 and planted into the selection field at the experimental garden at Nogales, Fifth Region, Chile in December 2006. The seedlings fruited for the first time in the southern hemisphere summer of 2006/2007 on floricanes and one seedling, designated 'HFM-7' and now known as 'Emilia', was selected on 11 Dec. 2007 for having early fruits that were large, sweet, and without noticeable aftertaste, and the plant was also thornless.

'Emilia' was first asexually propagated by taking root cuttings from the original plant which was growing in a field in Nogales, Fifth Region, Chile. 'Emilia' was dug-up completely and asexually propagated from the root pieces and by dividing the crown of the plant into individual canes. 'Emilia' has also been put into in vitro culture in Macul, Santiago, Chile. The methods of asexual reproduction used for the claimed variety yielded plants that are true to type in successive generations of asexual reproduction.

The growing location for many of the observations herein was Nogales, Fifth Region, Chile, in about 2007-2012. The date of the many of the observations was Dec. 11, 2007; other observations were obtained over two fruiting cycles in Chilean summer 2010/2011 and summer 2011/2012. Yield, overall plant health and vigor, fruit quality (at harvest and post-harvest) were further evaluated and informal taste tests were performed. 'Emilia' was above average on all characteristics evaluated and ranked among the top three of ten genotypes in taste tests.

General description: Plants of 'Emilia' have high vegetative vigor, similar to the variety 'Tupy'. The canes are completely thornless, have a green background color with a prominent reddish blush when exposed to light, erect in habit, and only produce flowers and fruits on previous-year's canes (i.e. floricane fruiting). 'Emilia' is a productive variety, similar to 'Tupy' in yield, the fruits are smaller than 'Tupy', with good flavor, high firmness, with almost no color regression (druplets turning from black to red) in cold storage, and the fruits have very little leakage of juice in post-harvest, which indicates that they are firm and will resist post-harvest decay.

Growth: Plants have high vegetative vigor, erect growth habit. Primocanes emerge both from the crown of the plant as well as from the roots (as suckers).

Growth rate: The growth rate is rapid, with canes reaching 1.5 meters in heights within one month of emergence from the soil in the spring.

Productivity: High.

Cold hardiness: Ultimate cold hardiness is unknown, but in Chile dormant plants have resisted midwinter lows of −7° C. without damage.

Branching height of the plants: Unknown (they are always pinched to induce branching and never left to grow to their own devices).

Canes:

*General description*.—Thornless, vigorous, very erect, thick diameter relative to other varieties ('Navaho' and 'Tupy').

*Cane diameter* (*indicate point of measurement*).—Floricane: Base: 1.87 cm. Midpoint: 1.55 cm. Terminal: 0.68 cm. Immature primocane: Base: 1.32 cm. Midpoint: 0.84 cm. Terminal: 0.44 cm. Mature primocane: Base: 1.76 cm. Midpoint: 1.09 cm. Terminal: 0.54 cm.

*Cane length*.—Floricane: approximately 2 meters, if not pinch-pruned. Mature primocane: approximately 2 meters, if not pinch-pruned.

*Cane texture*.—Floricane: Smooth. Immature primocane: Smooth. Mature primocane: Smooth.

*Internode length*.—Base: 12.57 cm. Midpoint: 6.61 cm. Terminal: 3.31 cm.

*Thorn density/30 cm*.—Base: 0. Midpoint: 0. Terminal: 0.

*Primocane color*.—Base: Yellow-green Group 146-B with occasional reddish streaks (Greyed-purple Group 183-B) where sunlight hits the cane. Midpoint: wine red color (Greyed-purple Group 183-B) on green background (Yellow-green Group 146-B). Terminal: wine red color (Greyed-purple Group 183-B).

*Immature primocane color*.—Base: Greyed-purple Group 183-B over a green background (Yellow-green Group 146-B). Midpoint: Greyed-purple Group 183-B. Terminal: Greyed-purple Group 183-B.

*Floricane color*.—Base: reddish brown (Greyed-orange Group 174A). Midpoint: reddish brown (Greyed-orange Group 175A) over green background (Yellow-green Group 146B). Terminal: reddish brown (Greyed-orange Group 175A) over green background Yellow-green Group 146B).

*Date of primocane emergence*.—Primocanes emerge during the first two weeks of October (in the southern Hemisphere at 32° 45' S. Lat., 220 m elev.) and continue emerging until the second week of December.

*Date of budbreak*.—Vegetative budbreak occurs from the 10th to the 20th of September (in the Southern Hemisphere at 32° 45' S. Lat., 220 m elev.).

*Number of new canes*.—A well-established plant (i.e. one that has been in the ground for 2 or 3 years) will emit an average of 4 new canes each year.

*Number of branches on dormant cane*.—If left unpruned, a primocane (which of course becomes a floricane once it goes dormant) will have no branches. However, in practice, the primocanes are always pinch-pruned at approximately 1.2 m in height to force lateral branching, which results in an average of 8 branches.

*Predominate distribution of branches*.—The branches, where stimulated by pinch-pruning, are in the apical zone of the cane.

Foliage:

*General description*.—Leaves are pentafoliate with abaxial trichomes, soft to the touch. The adaxial surface of the leaves have fewer trichomes and are rugose to the touch. Leaflets are green in color, but the adaxial side is a darker shade of green than the abaxial side. The leaflets are doubly serrate. There are no spines on any part of the leaf. The petioles and petiolules are wine red in color.

*Leaves*.—Width: 15.22 cm. Length: 18.88 cm (including petiole). Number of leaflets: 5 to 7. Shape: Palmately Compound.

*Leaflet*.—Width: 5.50 cm. Length: 8.85 cm (including petiolules). Margin: Doubly Serrate. Shape: Base: Cuneate. Apex: Acute to broadly acuminate. Shape: Ovate. Surface: Glabrescent and matte (opaque, ie not brilliant). Color: Base Adaxial: Green (Yellow-green Group 146-A) with the central vein of lighter green color (Yellow-green Group 146-B). Base Abaxial: Green (Yellow-green Group 146-B), but of a lighter shade than the adaxial side, with yellowish colored veins (Yellow-green group 144-B). Midpoint Adaxial: Green (Yellow-green Group 146-A), veins of the same color and shade. Midpoint Abaxial: Green (Yellow-green Group 146-A), but of a lighter shade than the adaxial side, yellowish colored veins (Yellow-green Group 146-C). Terminal Adaxial: Green (Yellow-green Group 146-A), with the veins being the same color and shade. Terminal Abaxial: Green (Yellow-green Group 146-D), but a lighter shade than the Adaxial side, with the veins being the same color. Note: on the adaxial side of the expanding new leaves, the tips of the serrations (margin) edge may display a reddish color (Greyed-purple Group 183-B).

*Petioles*.—Length: 8.92 cm. Color: wine red color (Greyed-purple Group 183-B). Diameter: 2-3 mm. Texture: Glabrescent.

*Petiolules*.—Length: 1-4 cm. Color: Wine red color (Greyed-purple Group 183-B). Diameter: 1-2 mm. Texture: Glabrescent.

*Stipules*.—Diameter: average 2 mm diameter. Texture: smooth. Color Greyed-Red Group 179B.

Flowers:

*Primocane*.—N/A (Primocanes have no flowers).

*Floricane*.—Date of bloom: (Southern Hemisphere). 10% bloom: 15th of September. 50% bloom: 25th of September. Last bloom: First week of October. Petal color: White (Group NN155 A-B). Reproductive organs: Stamens: Erect, numerous. Pistils: Numerous Pollen: Fertile and abundant. Ovary: Superior. Flower diameter: 3-4 cm. Petal size: Width: 1.2 cm. Length: 1.5 cm. Average number flowers per cluster: 10. Average number of petals per flower: 6. Peduncle length: 3-4 cm. Peduncle color: Yellow-green Group 146-B.

Fruit:

*General description*.—'Emilia' fruits are large, sweet, without bitter aftertaste common to blackberries. There is little color change (reversion) in drupelets from black to red in postharvest cold storage and the fruits can be stored for up to seven days. There is little to no incidence of post-harvest decay or rot (during seven days of storage at 5° C.).

*Primocane*.—N/A.

*Floricane*.—Average first ripe date: 23rd of November (7 days before 'Tupy'), the fruiting period lasts for 40 days. Size: Medium (6.1 grams on average). Diameter: Equator: 1.75 cm. Base pole: 1.81 cm. Terminal pole: 1.72 cm. Length: 2.81 cm. Shape: Oblong (Elongate). Drupelet size: Medium, 0.44 cm. Drupelet number: not measured. Color: Black Group 203-B. Seed size: not measured. Firmness: Firm. Flavor: Sweet with no bitter aftertaste. Soluble solids: 12.6° brix. pH: Not measured. Acidity: 0.75%. Processed quality: Not evaluated. Uses: The primary use is for fresh market sales due to its excellent post-harvest behavior. Prickles: None.

Typical market use: Fresh Market.

Keeping quality: Good.

Shipping quality: Good.

What is claimed is:

1. A new and distinct cultivar of Blackberry plant named 'Emilia' as described and shown herein.

* * * * *